United States Patent
Gross et al.

(10) Patent No.: US 7,563,240 B2
(45) Date of Patent: Jul. 21, 2009

(54) HAEMODIALYSIS DEVICE

(75) Inventors: Malte Gross, Niederwerrn (DE);
Andreas Wuepper, Weiterstadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 10/552,716

(22) PCT Filed: Feb. 17, 2004

(86) PCT No.: PCT/EP2004/001457
§ 371 (c)(1),
(2), (4) Date: Oct. 11, 2005

(87) PCT Pub. No.: WO2004/089440
PCT Pub. Date: Oct. 21, 2004

(65) Prior Publication Data
US 2006/0200064 A1    Sep. 7, 2006

(30) Foreign Application Priority Data
Apr. 11, 2003   (DE) ................. 103 17 024

(51) Int. Cl.
*A61M 37/00*   (2006.01)
(52) U.S. Cl. .................. 604/5.01; 604/1.04; 604/5.02; 604/6.11; 604/6.14
(58) Field of Classification Search ............. 604/6.11, 604/6.14, 4.01, 5.01, 5.02; 422/44, 45
See application file for complete search history.

(56) References Cited

U.S. PATENT DOCUMENTS

| | | | |
|---|---|---|---|
| 4,202,760 A * | 5/1980 | Storey et al. ................ 252/364 |
| 5,100,554 A | 3/1992 | Polaschegg | |
| 5,110,477 A | 5/1992 | Howard et al. | |
| 5,567,320 A | 10/1996 | Goux et al. | |
| 5,744,031 A | 4/1998 | Bene | |
| 6,126,831 A | 10/2000 | Goldau et al. | |
| 6,156,002 A | 12/2000 | Polaschegg et al. | |
| 6,187,199 B1 | 2/2001 | Goldau | |
| 6,325,774 B1 | 12/2001 | Bene et al. | |
| 6,860,866 B1 | 3/2005 | Graf et al. | |
| 6,939,471 B2 | 9/2005 | Gross et al. | |

FOREIGN PATENT DOCUMENTS

| | | |
|---|---|---|
| DE | 39 38 662 A1 | 7/1991 |
| DE | 197 47 360 A1 | 4/1999 |
| DE | 102 12 247 C1 | 12/2003 |
| EP | 0 658 352 A1 | 6/1995 |
| EP | 0 911 043 A1 | 4/1999 |
| EP | 1 062 960 A2 | 12/2000 |
| WO | WO 98/32476 | 7/1998 |
| WO | WO 00/02604 | 1/2000 |

* cited by examiner

*Primary Examiner*—Jacqueline F. Stephens
(74) *Attorney, Agent, or Firm*—Jacobson Holman PLLC

(57) ABSTRACT

A blood purification device has a blood purification element divided into two chambers by a semipermeable membrane, with a first chamber as part of a dialysis fluid loop and a second chamber as part of an extracorporeal blood loop. By virtue of an analysis unit operatively connected to a sensor in the dialysis fluid loop, the device provides simple and uncomplicated determination of the blood purification performance of the blood purification element for a second material by derivation from a previously established blood purification performance for a first material. In this way, the device also determines the blood concentration of the second material during the blood treatment through measurements in the dialysis fluid without intervention in the treatment sequence.

17 Claims, 1 Drawing Sheet

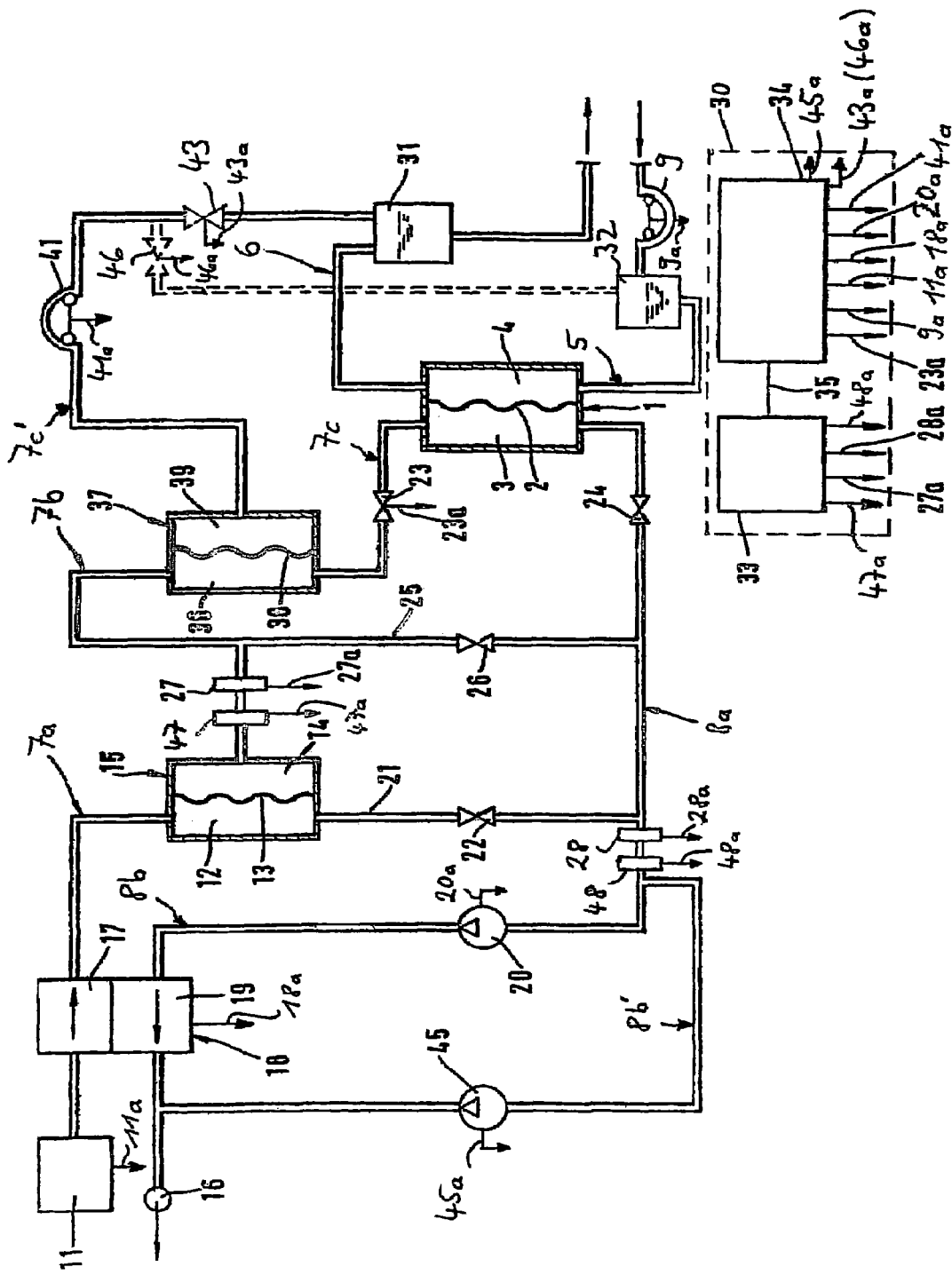

HAEMODIALYSIS DEVICE

This is a nationalization of PCT/EP04/001457 filed Feb. 17, 2004 and published in German.

BACKGROUND OF THE INVENTION

1. Field of the Invention

The present invention relates to the field of blood treatment devices having a blood purification element divided into two chambers by a semipermeable membrane, whose first chamber is part of a dialysis fluid loop and whose second chamber is part of an extracorporeal blood loop. The device has a dialysis fluid supply line for supplying fresh dialysis fluid to the first chamber and/or into the blood loop, a dialysis removal line for removing used dialysis fluid from the first chamber, a control unit for controlling the blood treatment device, an analysis unit, and at least one sensor, connected to the analysis unit, on at least one of the blood loop or dialysis fluid loop to detect the concentration of a first material which may penetrate the semipermeable membrane. The analysis unit is capable of determining the blood purification performance L1 of the blood purification element for the first material on the basis of the measurement values of the at least one sensor.

2. Description of the Prior Art

Various methods are used in kidney replacement treatment. In some of these methods, blood is continuously removed from a patient during the treatment and fed into an extracorporeal loop. There it flows through a blood purification element in order to then be returned to the patient. The blood purification element typically has a filter element divided into two chambers by a semipermeable membrane, one chamber of which blood flows through. Currently, filter elements which contain many thousands of hollow fibers, through which blood flows, are typically used above all for this purpose.

In hemodialysis, a purification fluid (dialysis fluid), which absorbs the materials such as urea to be removed from the blood by diffusion and, in regard to other materials such as electrolytes, which are to be left in the blood, has a composition similar to a healthy blood count, flows through the other chamber. Fluid volumes to be removed are also removed from the blood chamber to the dialysis fluid chamber of the filter element using a component which controls the ultrafiltration.

In hemofiltration, the other chamber of the filter element, which is referred to in the following as the first chamber, does not have a second fluid flowing through it completely. Rather, ultrafiltrate is only fed via the membrane into this chamber, which is then removed via an ultrafiltrate drain. In this case, the quantity of fluid removed is kept well over that which must be removed from the patient to achieve his dry weight. In this way, materials such as urea which are to be removed are carried off with the ultrafiltrate in an appreciable amount through convection. Simultaneously, almost the entire quantity of fluid is replaced by a substitution fluid which is returned to the patient at a suitable point via the extracorporeal loop.

Since convection and diffusion are able to remove molecules of different sizes through the membrane with different degrees of effectiveness, the combination of both methods in the form of a hemodiafiltration treatment is also used. For this purpose, modern dialysis machines offer the possibility of changing between these modes of treatment without complex modification being necessary. In this case, some known devices have the possibility of the dialysis and the substitution fluids being prepared online from water and appropriate concentrate by the machine during the treatment. For these devices, it is no longer necessary to keep ready enormous quantities of these fluids (up to approximately 200 liters) in the form of bags. Such a device is the object of European Patent Application 0 930 080 A1, for example.

In order to be able to monitor the success of kidney replacement treatment, the determination of treatment parameters on such blood purification devices, particularly the blood purification performance of the blood purification element, is of great interest. The clearance or dialysance of the blood purification element is typically specified as the blood purification performance.

The clearance K is defined as the blood flow which is completely freed of a substance (e.g., urea) by the blood purification element. In this case, it is assumed for a hemodialysis treatment that the dialysis fluid does not contain the substance to be removed when it enters the dialyzer. The clearance is a function of the area and material of the dialyzer and the particular operating conditions (blood flow, dialysis fluid flow, and ultrafiltration flow). The clearance occurs both through diffusion and through convection via the membrane of the filter element—the dialyzer.

The concept of clearance may also be expanded to substances such as sodium ions, for example, which are already present in the dialysis fluid. In this case, the term used is dialysance D. It is defined as the blood flow which is brought completely to the concentration level in the dialysis fluid.

The dimensionless variable Kt/V may be calculated from the clearance K, t being the duration of treatment and V being the distribution volume of the substance in the human body. Kt/V for urea is widely used as a measure for the efficiency of a dialysis treatment.

The measurement of the urea concentration is, however, relatively complicated. It either requires blood samples to be taken, which is unpleasant for the patient and in addition does not allow rapid, automated analysis, or it is still quite complicated as a measurement in the used dialysis fluid.

A current alternative is the determination of the ionic dialysance. The basic principle of these measurements is based on the fact that urea and small ions such as $Na^+$, etc. have nearly identical diffusion behaviors. The concentration of these ions may be determined easily in the dialysis fluid with the aid of measurements of the electrical conductivity, which may be determined using relatively simply constructed measurement cells. Instead of the urea clearance, therefore, the ionic dialysance is primarily determined. This may then be set equal to the urea clearance, due to the identical diffusion behavior to be expected.

Since, for hemodialysis, the clearance only represents a special case of dialysance for the case in which the relevant substance is not present in the dialysis fluid, it is to be included as synonymous with the term dialysance in the following.

In the related art, there are diverse publications on the calculation of dialysance (e.g., J. Sargent and F. Gotch, in: Replacement of Renal Functions by Dialysis, 4th edition, edited by C. Jacobs et al., Kluwer, Dordrecht, 1996, p. 39 et seq.). Without ultrafiltration, it may be expressed in the dialysate-side form in the following form:

$$D = Qd \frac{Cdo - Cdi}{\alpha Cbi - Cdi}, \qquad (1)$$

in which

Qd: dialysis fluid flow,

Cdo: concentration of the material observed in the dialysis fluid removed,

Cdi: concentration of the material observed in the dialysis fluid supplied,

Cbi: concentration of the material observed in the blood flowing in the extracorporeal loop (only the volume component in which this material is effectively dissolved to be observed), α: Gibbs-Donnan factor.

The Gibbs-Donnan factor takes the fact into consideration that on the blood side, charged ions such as $Na^+$ are partially bound on oppositely charged proteins, which are not accessible to the dialyzer. This effect has the result that in the diffusive equilibrium (with vanishing flows) in the blood plasma, a somewhat higher ion concentration would result than in the dialysis fluid, since an electrical field counteracts the diffusion. For the case, which is especially relevant in practice, of sodium ions in blood plasma, α is approximately 0.95. If precision is not required, this factor may also be ignored.

In equation 1, all dimensions except for Cbi may be measured easily. For this purpose, it is sufficient to position two conductivity measurement cells in the dialysis fluid loop, which each determine the conductivities at the inlet and outlet of the dialyzer. The latter may be easily converted into the concentrations Cdi and Cdo. If the concentration Cdi is also preset and therefore known, because precisely defined fluids are used, for example, the measurement of Cdi may even be unnecessary. The dialysis fluid flow Qd is typically preset by the hemodialysis machine and is therefore also known. Otherwise, additional appropriate sensors may also be provided, of course.

However, conductivity measurements on the blood side are problematic for practical reasons. It is nonetheless possible to eliminate the term Cbi by changing the concentration Cdi. This may be performed in the form of a concentration step or a bolus, for example. The first is described in German Patent Application 39 38 662 A1, and the latter in German Patent Application 197 47 360 A1 or WO 00/02604 A1 (explicit reference is hereby made to these publications). Both possibilities are to be considered in the following as alternatives for a change of the concentration in a fresh fluid which is necessary for the blood treatment. The dialysance may then be determined as follows:

$$D = Qd\left(1 - \frac{Cdo2 - Cdo1}{Cdi2 - Cdi1}\right) = Qd\left(1 - \frac{\Delta Cdo}{\Delta Cdi}\right), \quad (2)$$

in which

Cdi1,2: Cdi before and after (step) or outside and during (bolus) the change

Cdo1,2: Cdo before and after (step) or outside and during (bolus) the change.

In the case of a step change, ΔCdi and/or ΔCdo represent simple differences, in the case of the bolus method, they are understood as the change relative to a base level integrated over the bolus.

With the aid of D, Cbi may now also be determined using equation (1). In this case, it would be considered equivalent to first determine Cbi as the parameter to be determined from an equation corresponding to the equation (2), which arises from equation (1) if D is eliminated.

Further methods are known in the related art, such as in WO 98/32476 A1 or European Patent Application 0 658 352 A1, which do not explicitly use the equation (2) to determine D, but are, in the final analysis, always based on the principle of producing a change of a physical-chemical property Cdi and retaining the corresponding change Cdo in order to obtain information about the physical-chemical property Cbi on the blood side or the blood purification performance D.

Sometimes, the mass exchange or filter coefficient k0A, which has a fixed relationship to the dialysance D, is also used for describing the blood purification performance of a blood purification element such as a dialyzer. The coefficient k0A is determined solely by the material observed and the dialyzer membrane used, but not by treatment parameters such as blood flow, dialysis fluid flow, or ultrafiltration flow. It is the product of the parameter k0, which is a function of the membrane, and the total area of the membrane A. In this case, k0 corresponds to the diffusion flow of the material observed per area unit of the membrane, divided by the concentration gradient on the membrane. K0A may then be interpreted as the maximum possible dialysance in the ideal case of purely diffusive transport with infinitely large dialysis fluid flow and blood flow.

The coefficient k0A for a material may be determined on the basis of the measurement of the dialysance D according to equation (3):

$$k0A = \frac{QbQd}{Qd - Qb} \ln \frac{Qb(D - Qd)}{Qd(D - Qb)} \quad (3)$$

In the related art, methods which allow determination during a hemodialysis treatment are specified exclusively in this case. There are also statements therein—sometimes differing—as to how the ultrafiltration flow Qf withdrawn from the blood during a hemodialysis treatment may be taken into consideration in the equations (1) or (2). An example of this is European Patent Application 1 062 960 A2, according to which Qd is replaced by the sum of the flows Qd and Qf. However, for a hemodialysis treatment the ultrafiltration flow Qf is very small in comparison to the dialysis fluid flow Qd and also to the blood flow Qb, i.e., it is a relatively small interfering effect. Thus, for example, typical values are Qf=15 ml/minute, Qd=500 ml/minute, and Qb=300 ml/minute.

Similar restrictions apply for the blood flow Qb in equation (3) as for the concentration Cbi in equation (1). Sometimes, only the volume component of the blood in which the material observed is effectively dissolved must be considered in equation (3). Depending on the material, this may be the blood water component with or without blood cells, for example. The ways of deriving the component flow in relation to the complete blood flow on the basis of average, assumed, or measured data via the blood composition (hematocrit, proteins, etc.) are sufficiently known to one skilled in the art in this case (e.g., J. Sargent and F. Gotch, in: Replacement of Renal Functions by Dialysis, 4th edition, edited by C. Jacobs et al., Kluwer, Dordrecht, 1996, p. 41 et seq.), so that further explanation will be dispensed with at this point.

However, for kidney replacement treatment, the knowledge of the performance of the blood purification element is just as much of interest when it is a hemofiltration treatment—whether alone or in combination with a hemodialysis treatment in the form of a hemodiafiltration treatment.

As was described in the previously filed German Patent Application 10212247.4, to the content of whose disclosure explicit reference is made here, methods developed for hemodialysis may be transferred to hemofiltration and hemodiafiltration if the dialysis fluid flow Qd includes the substitution fluid flow and the concentration for the fresh dialysis fluid is equal to the concentration for the substitution fluid. In this case, the dialysis fluid flow Qd in the equations (1) and (2) is to be set to the sum of the flow of dialysis fluid flowing in the first chamber of the hemodialyzer, the flow Qs of the substitution fluid, and the total ultrafiltration flow Qf to be withdrawn from the blood.

Using the previously known methods, it is possible—as described above—to determine the concentration Cbi of a first material in the blood flowing into the blood purification unit and/or to determine the blood purification performance of the blood purification unit on the basis of concentration measurements in the dialysis fluid, the concentration of the first material in the dialysis fluid having to be changed during the method, however. This requires a certain minimum measurement time for the corresponding adjustment or change of the concentration. It is especially disadvantageous that, using these methods, materials which do not generally occur in the fresh dialysis fluid (e.g. creatinine or phosphate) or whose variation may be critical to patient compatibility (e.g., potassium), are not accessible.

Other methods are known, like that described in U.S. Pat. No. 6,126,831, in which, for dialysate measurement of blood components, the dialysis fluid is slowed or even stopped in such a way that the concentration of both fluid equalizes, so that the concentration in the dialysis fluid corresponds directly to the concentration Cbi in the blood. Methods of this type are also time-consuming and require direct intervention in the blood treatment.

The present invention is therefore based on the object of providing a device which, without additional intervention in the blood treatment performed using a blood purification element, allows determination of a further, different blood purification performance of the blood purification element in relation to a further material and therefore opens up the possibility of also determining the blood concentration of this further material.

SUMMARY OF THE INVENTION

This object is achieved by the features of claim 1. Advantageous embodiments are the object of the subclaims.

The present invention is based on the observation that current hemodialysis devices often have the proven capability of determining the blood purification performance of the blood purification element—in this case the dialysance of the dialyzer—in relation to a first material. In this case, as described above, the sodium ion dialysance may be determined with the aid of a change of the concentration in the fresh dialysis fluid. In this case, it is now possible to determine the second blood purification performance, which is different from the first blood purification performance, for a second material, without a further measurement method being necessary. Rather, on the basis of relationships between the two blood purification performances which are stored in an analysis unit and which go beyond a mere identity assignment for identical blood purification performances as in the case of sodium ions and urea, the second blood purification performance may be determined directly. This relationship, which may be determined in advance in laboratory experiments, is solely a function of the type of blood purification element used.

At the same time, the present invention has the advantage that through the previously performed measurement of the blood purification performance for a first material, individual adjustment of the actual value of the blood purification performance for a second material is made possible, which takes the change of the blood purification performance of a specific blood purification element during a blood treatment into consideration sufficiently, for example. In this regard, the present invention goes beyond the mere calculation of the blood purification performance for different molecule sizes through the membrane characteristic data.

An important refinement of the present invention is that, with the aid of a sensor for measuring the concentration of the second material in the used dialysis fluid and—if the concentration of this material in the fresh dialysis fluid is not known—a corresponding sensor for the fresh dialysis fluid, the concentration of this material in the blood flowing to the blood purification element may be determined with the aid of the previously determined blood purification performance, without an intervention in the dialysis fluid concentration or the delivery speeds of the individual fluids being necessary. This is possible without restriction for all materials whose concentration in the dialysis fluid may be determined using measurement technology—independently of their presence in the fresh dialysis fluid or a restricted possibility of variation.

The present invention and an exemplary embodiment of a hemodiafiltration device according to the present invention are described in greater detail in the following on the basis of the drawing. In this case, the drawing shows a schematic illustration of this embodiment.

BRIEF DESCRIPTION OF THE DRAWINGS

The drawing FIGURE illustrates a hemodialysis device according to an embodiment of the present invention.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The core of the hemodiafiltration device is the hemodialyzer 1. The hemodialyzer 1 is divided by a semipermeable membrane 2 into two chambers 3 and 4, of which the first chamber 3 is a part of a dialysis fluid loop and the second chamber 4 is a part of an extracorporeal blood loop.

The extracorporeal blood loop includes, in addition to other typical components (not shown in greater detail), a blood supply line 5 having a blood delivery pump 9 and an arterial bubble trap 32 for supplying blood from a patient to the chamber 4 and a blood removal line 6 having a venous bubble trap 31 for returning the blood to the patient.

The dialysis fluid loop contains a dialysis fluid removal line, divided into sections 8*a*, 8*b*, from which an ultrafiltration removal line 8*b*' branches off. The section 8*a* leads out of the first chamber 3, a valve 24 being provided to shut off this outlet line of the hemodialyzer. At the end of the section 8*a*, a first downstream sensor is provided, implemented as a conductivity measurement cell 28 for detecting the electrical conductivity, using which the ion concentration and/or predominantly the sodium concentration C1do may be determined in a known way. For this purpose, the measurement cell 28 is connected to a central analysis and control unit 30 via a data line 28*a*.

The dialysis fluid pump 20, which does not have any special requirements in regard to precision, is incorporated into section 8b. It must merely provide sufficient delivery capacity so that the first balance chamber half 19 of a balance chamber 18, which is connected into the section 8b, may be filled within predetermined times. The balance chamber 18 is used to ensure that the section 8b only has a part of the dialysis fluid flow removed flowing through it, which corresponds to the fluid flow supplied to the hemodiafiltration device (substitution fluid having flow Qs and fresh dialysis fluid having flow Qd). In this case, the balance chamber 18 expediently includes two balance chambers connected in parallel, so that a practically constant flow may be ensured. For the sake of simplicity, the second balance chamber and the diverse intake and outlet valves are not shown in the drawing.

A delivery pump 45, implemented as a volumetric pump, preferably a membrane pump, is provided in the section 8b'. Using this pump, the ultrafiltration flow Qf to be removed, which is to be withdrawn from the patient overall, is conveyed. The balance chamber 18 and the pumps 20 and 45 are connected using corresponding control lines 18a, 20a, and 45a to the analysis and control unit 30.

The sections 8b and 8b' finally discharge into a drain 16, it being unimportant whether or not both sections join together in the device as shown.

Fresh substitution and/or dialysis fluid is provided by a fluid source 11, which is part of a dialysis fluid preparation system. Various alternatives are available to one skilled in the art for implementing the fluid source. Besides providing the finished solution in bags, there is particularly the preparation of the fluid from water and concentrate in the hemodiafiltration device itself. For this purpose, the device contains diverse measurement and control elements, which will not be explained at this point and which are well-known.

The dialysis fluid loop also includes the following components: The fresh dialysis fluid flows from the fluid source 11 through a first section 7a of a dialysis fluid supply line, which the sections 7b and 7c adjoin. The second balance chamber half 17 of the balance chamber 18 is connected into the section 7a. It finally discharges into the first chamber 12 of a first sterile filter 15, which is divided into two chambers 12 and 14 by a semipermeable membrane 13. After passing the membrane 13, the fluid leaves the second chamber 14 of the first sterile filter via the section 7b of the dialysis fluid supply line, which leads to the first chamber 36 of a second sterile filter 37, divided into two chambers 36 and 39 by a semipermeable membrane 38. A first upstream sensor 27, corresponding to the first downstream sensor 28, is provided in the section 7b for detecting the electrical conductivity of the fluid flowing through the sensor, which is in turn connected using a data line 27a to the analysis and control unit 30.

The substitution fluid passing the membrane 38 leaves the second chamber 39 of the sterile filter 37 via the substitution fluid line 7c'. A delivery pump 41 is provided in this section for delivering the substitution fluid flow Qs. A shutoff valve 43 is provided before the substitution line 7c' discharges into the venous bubble trap 31 (post-dilution). Alternatively or additionally (shown using dashes), the substitution fluid line 7c' may discharge into the arterial bubble trap (pre-dilution). A further shutoff valve 46 would then be provided in this section.

A section 7c of the dialysis fluid line leads from the first chamber 36 of the second sterile filter 37 to the first chamber 3 of the hemodialyzer 1. The section 7c may be closed by a shutoff valve 23, which is connected via the control line 23a to the analysis and control unit 30. Whether a blood treatment is to be performed solely as a hemofiltration treatment (valve closed) or as a part of a hemodiafiltration treatment (valve open) may thus be controlled using this valve. It is also possible to change the treatment mode during a treatment. Furthermore, a pure hemodialysis treatment may be performed at any time by stopping the pump 41 and closing the valves 43 and 46.

With the aid of the valves 43 and 46 (control via lines 43a and 46a) is possible to change between pre-dilution and post-dilution or even to allow both simultaneously. For this purpose, the valves 43 and 46 may be used for flow control or may be supplemented/replaced by separate delivery means in order to detect the distribution of the substitution fluid flow Qs.

For safety and purification functions not described in greater detail here, a first bypass line 21 is also provided, which connects the first chamber 12 of the first sterile filter 15 to the section 8a of the dialysis fluid removal line and which may be closed by a valve 22 during normal operation. This also applies for a second bypass line 25, which branches off of the section 7b of the dialysis fluid supply line and also discharges upstream into the section 8a of the dialysis fluid removal line. The second bypass line may be closed by a valve 26.

The hemodiafiltration device also contains an analysis and control unit 30, which in turn includes an analysis unit 33 and a control unit 34, which are connected to one another by a data line 35. The control unit is connected via the control lines 9a, 11a, 18a, 20a, 23a, 41a, 43a, 45a, and 46a to the diverse control elements of the hemodiafiltration device, in order to be able to control their operation. In this case, only the control elements/lines which are necessary to understand the present invention were cited.

The analysis unit is connected via data lines to several sensors. In this case, these are particularly the two conductivity sensors 27 and 28. Furthermore, a second upstream sensor 47 and a second downstream sensor 48 are provided for detecting the concentration of a second material such as potassium, calcium, phosphate, creatinine, or glucose in the dialysis fluid loop. Greatly varying embodiments for implementing second sensors 47 and 48 of this type, which are tailored to the purpose, are well-known to one skilled in the art. The sensors 47 and 48 are connected via data lines 47a and 48b to the analysis unit 33. The use of a second upstream sensor may be unnecessary in the case in which the concentration of the second material in the fresh dialysis fluid is known. This may particularly be exploited with high precision if the second material is not even contained in the fresh dialysis fluid, for bodily excretion products such as creatinine, for example.

The volume of a balance chamber filling is known very precisely. The flow Qs+Qd may be determined very precisely via the frequency of the balance chamber pulses. The pump 45 is volumetric and may therefore also be used—in this case as a membrane pump via the frequency of the pump strokes and the known stroke volume—to determine the flow Qf. This removes imprecisions which may arise, for example, through a substitution fluid pump 41 designed as a roller pump, whose delivery quantity may vary in a certain range due to tolerance variations of the pump hose segment and also through charging pressure variations.

The device according to the present invention is capable of performing the following method steps. Therefore, for the sake of simplicity, it is initially assumed that during the detection of the measured values only a hemodialysis treatment is performed, without ultrafiltration, i.e., Qs=Qf=0.

The fluid source 11 is driven in such a way that it prepares dialysis fluid having a sodium concentration C1di1. This concentration is recorded via the first upstream sensor 27 and transmitted to the analysis unit 33. The fluid flows Qb and Qd are adjusted and the valves 23, 43, and 46 are opened and/or closed at the delivery devices/pumps 9, 18, 20, 41, and 45 for the hemodialysis type of operation. The values for Qb and Qd are also transmitted from the control unit 34 to the analysis unit 33. The sodium concentration values C1do1 are recorded by the first downstream sensor 28 and transmitted to the analysis unit 33.

At a time which was automatically provided by the control sequence or caused for another reason (e.g., manually), the fluid source 11 performs a change of the sodium concentration of the dialysis fluid, upon the command of the control unit 34, in bolus form, for example, i.e., the sodium concentration is changed briefly and then again assumes the starting value. The corresponding concentrations C1di2 and C1do2 are recorded and transmitted to the analysis unit 33. After the bolus dies out, the analysis unit 33 determines the ion dialysance and/or sodium ion dialysance D1 of the hemodiafiltration device as the blood purification performance L1 of the blood purification element 1 for a first material in the known way with the aid of equation (2). This value may be displayed via a display unit (not shown), which is typically a part of blood treatment devices of this type anyway. The measured value dialysance D1 is indicated in the following as effective dialysance D1eff, in order to be able to distinguish it from the theoretical dialysance D1th to be expected on the basis of the knowledge of the membrane material.

To determine the blood purification performance L2 of the blood purification element 1 for a second material, the analysis unit 33 is capable according to the present invention of applying one of the two methods described in the following. Both methods are based on the mass exchange coefficients k0A1,2 previously determined by the analysis unit for the two materials to be observed, which have a fixed relationship to one another:

$$k0a2 = f \cdot k0a1 \quad (4).$$

For a dialysis filter distributed by the applicant under the name F60, for example, for urea (and/or sodium) as the first material and for potassium as the second material, values of k0A1=734.7 ml/min. and f=1.08 may be found. Either these values or the values of k0A1 and k0A2 are stored in the analysis unit 33.

With the aid of the known values, the analysis unit 33 may determine the corresponding theoretical dialysance values D1th and D2th by solving the equation (3), since the values for the blood flow Qb and the dialysis fluid flow Qd are also stored in the analysis unit 33. With the aid of the measured, effective dialysance value D1eff for sodium, the effective dialysance value D2eff for potassium may now be established using equation (5):

$$D2\textit{eff} = D1\textit{eff} \frac{D2th}{D1th}. \quad (5)$$

On the other hand, is also possible for the analysis unit 33 to first, on the basis of the measured dialysance D1eff for sodium, determine the corresponding effective mass exchange coefficient k0A1eff with the aid of equation (3). The stored values for f are then used for the purpose of determining the effective mass exchange coefficient k0A2eff for potassium using equation (4). This is then in turn, with the aid of equation (3), used to determine the effective dialysance D2eff to be determined for potassium. In contrast to the first method, in this case only the factor f, and not also the value for k0A1th, must be stored.

The stored values for k0A may be stored for a series of dialyzers, which differ solely in the active membrane area A, but have the same type of membrane, in such a way that only a membrane-specific value (such as k0) must be stored, while the other values may be calculated accordingly through the proportionality to A. This is not necessary for the second method, since the factor f is independent of the active membrane area A.

It is obvious that the calculations may be performed for any second material for which the corresponding data according to equation (4) exists. Thus, for example, for the F60 membrane, f=0.52 for glucose, f=0.71 for creatinine, and f=0.66 for phosphate.

After the analysis unit 33 has determined the dialysance D2eff as the blood purification performance of the blood purification element 1 in relation to the second material, this may also be made available to the user on a display unit.

In an especially advantageous embodiment of the present invention, the established value of D2eff is used to determine the concentration C2bi of the second material in the blood supply line 5. For this purpose, the measurement values of the second upstream and downstream sensors 47 and 48, which determine the concentrations C2di and C2do of the second material in the fresh and used dialysis fluid, are registered by the analysis unit 33. No intervention in the treatment sequence is necessary for this purpose. The analysis unit then determines C2bi by solving equation (1) for Cbi.

Both of the methods described for applying equation (4) lead to identical numerical results when used on "ideal" systems. However, in practical application, small deviations occur, whose causes are described in greater detail in the following.

One of the main causes for the deviations is the fact that in a real dialysis system, recirculation of purified blood occurs, through which the theoretically achievable dialysance Dth is reduced. Only the corresponding reduced effective dialysance Deff may be determined by measurement. The recirculation may occur in this case in the patient's vessels—typically an arteriovenous fistula—from which the blood is removed and then returned to. In this case, purified blood may return directly to the dialyzer 1. This fistula recirculation may, however, be largely avoided through a suitable selection of the blood flow Qb, as long as the blood flow Qb is smaller than the blood flow flowing to the fistula. A part of the purified blood returns directly as cardiopulmonary recirculation to the fistula via the circulatory system of the patient, however, without having gone through metabolism. This part of the recirculation occurs inherently and may not be avoided, although it is not a dominant effect.

The influence of recirculation on the dialysance or clearance is described by, among others, H. D. Polaschegg and N. W. Levin (in "Replacement of Renal Functions by Dialysis", 4th edition, edited by C. Jacobs et al., Kluwer, Dordrecht, 1996, p. 371 et seq.) Accordingly, the following relationship exists between the effective dialysance Deff, which is reduced by the recirculation R, and the corresponding dialysance Dth without recirculation for the same dialyzer and the same flow ratios:

$$Deff = Dth \frac{1-R}{1-R\left(1-\frac{Dth}{Qb}\right)}, \quad (6)$$

R indicating the proportion of the recirculation blood between 0 and 1 in the blood flow Qb. If the recirculation R is known (through other measurement methods), equation (6) may be taken into consideration to improve the precision of D2eff.

Further differences between the two calculation methods are caused because the parameters used, such as fluid flows or even the values for k0A and/or f, are only known within certain limits of error. This leads, due to the input of the actual value D1eff for the dialysance of the first material, to different resulting errors for D2eff, whose influence is limited, however, and which may be investigated beforehand through calibration measurements in the laboratory.

The present invention may be used not only for pure hemodialysis, but rather also in the case in which ultrafiltration (Qf>0) and/or hemodiafiltration (Qs>0) are not turned off. As described in the German Patent Application 10212247.4, not only the values for Qd and Qb, but also for Qf and Qs are transmitted to the analysis unit 33 via the line 35 for this purpose. The analysis unit 33 may then determine the diffusive part of the dialysance on the basis of equation (7):

$$Ddiff = \frac{Qb + \kappa Qs}{Qb - Qf - (1-\kappa)Qs}\left(\frac{Qb + \kappa Qs}{Qb}D - Qf - Qs\right), \quad (7)$$

in which K=1 for pre-dilution and K=0 for post-dilution. Subsequently, the membrane exchange coefficient k0A may be determined, for which only the diffusive part of the dialysance is relevant:

$$k0A = \frac{(Qb + \kappa Qs)Qd}{Qd - Qb - \kappa Qs}\ln\frac{\frac{Ddiff}{Qd} - 1}{\frac{Ddiff}{Qb + \kappa Qs} - 1} \quad (8)$$

Equation (8) corresponds to a generalization of equation (3).

The embodiment shown in the drawing has first and second upstream sensors 27 and 47 for measuring the concentrations C1di of the first material and C2di of the second material in the fresh dialysis fluid. As an alternative to these upstream sensors, the downstream sensors 28 and 48 may also be used to measure the concentration in the fresh dialysis fluid if the fresh dialysis fluid is conducted directly to the downstream sensors while bypassing the dialyzer. This may be performed by opening the bypass valves 22 or 26.

This alternate embodiment is not subject to special disadvantages, particularly for the measurement of the second material. Since the concentration of the second material in the fresh dialysis fluid remains constant in most cases, only one single measurement is necessary at the beginning of the treatment. However, if this concentration changes due to a controlled variation during a blood treatment, the measurement may be updated at any time by brief switching into the bypass. If the blood treatment device performs such a bypass switch periodically due to other method steps (e.g., to flush the first sterile filter 15), the measurement of the second material may be performed simultaneously without additional method steps.

The present invention therefore allows simple and uncomplicated determination of the blood purification performance of a blood purification element for a second material after the blood purification performance for a first material, which deviates therefrom, was determined previously. Furthermore, determination of the blood concentration of materials through measurements in the dialysis fluid is made possible, which was previously not possible due to the poor accessibility of the current blood purification performance of the blood purification element in regard to these materials. This allows blood treatment which is more bearable for the patient.

By determining the potassium concentration, arrhythmias may be avoided better during dialysis. The monitoring of the glucose concentration offers an important aspect for avoiding complications, particularly for diabetic patients. The knowledge of the calcium concentration in the blood is especially important if citrate is used as an anticoagulant. In this case, calcium must be infused into the blood from the line so that citrate is bound before the blood is returned to the patient. Care must be taken that the calcium concentration is not too high as a consequence. The knowledge of the phosphate concentration also represents important information, since, particularly in dialysis patients, there is the danger that too high a phosphate level will lead to deposits of calcium phosphate in the tissue.

Through the device according to the present invention, the corresponding measurement values are available directly during the blood treatment, without complicated analysis of blood samples in a laboratory being necessary.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

| | List of reference numbers |
|---|---|
| 1 | dialyzer |
| 2 | semipermeable membrane of the dialyzer |
| 3 | first chamber of the dialyzer |
| 4 | second chamber of the dialyzer |
| 5 | blood supply line |
| 6 | blood removal line |
| 7a | first section of the dialysis fluid line |
| 7b | second section of the dialysis fluid line |
| 7c | third section of the dialysis fluid line |
| 7c' | substitution fluid line |
| 8a | first section of the dialysis fluid removal line |
| 8b | second section of the dialysis fluid removal line |
| 8b' | ultrafiltrate removal line for fluid removal |
| 9 | blood pump |
| 11 | dialysis/substitution fluid source |
| 12 | first chamber of the first sterile filter |
| 13 | semipermeable membrane of the first sterile filter |
| 14 | second chamber of the first sterile filter |
| 15 | first sterile filter |
| 16 | discharge |
| 17 | second balance chamber half |
| 18 | balance chamber |
| 19 | first balance chamber half |
| 20 | dialysis fluid circulation pump |
| 21 | first bypass line |
| 22 | first bypass valve |
| 23 | dialysis fluid supply valve |
| 24 | dialysis fluid removal valve |
| 25 | second bypass line |

-continued

List of reference numbers

| | |
|---|---|
| 26 | second bypass valve |
| 27 | first upstream sensor for detecting the conductivity of the fresh dialysis fluid to determine the sodium ion concentration |
| 28 | first downstream sensor for detecting the conductivity of the used dialysis fluid to determine the sodium ion concentration |
| 30 | analysis and control unit |
| 31 | venous bubble trap |
| 32 | arterial bubble trap |
| 33 | analysis unit |
| 34 | control unit |
| 35 | data line between analysis unit and control unit |
| 36 | first chamber of the first sterile filter |
| 37 | second sterile filter |
| 38 | semipermeable membrane of the second sterile filter |
| 39 | second chamber of the second sterile filter |
| 41 | substitution fluid pump |
| 43 | post-dilution valve |
| 45 | pump for fluid removal |
| 46 | pre-dilution valve |
| 47 | second upstream sensor for detecting the concentration of a second material in the fresh dialysis fluid |
| 48 | second downstream sensor for detecting the concentration of the second material in the used dialysis fluid |

What is claimed is:

1. A blood treatment device comprising a blood purification element, divided into two chambers by a semipermeable membrane, whose first chamber is part of a dialysis fluid loop and whose second chamber is part of an extracorporeal blood loop,
   a dialysis fluid supply line for supplying fresh dialysis fluid to the first chamber and/or into the blood loop,
   a dialysis fluid removal line for removing used dialysis fluid from the first chamber,
   a control unit for controlling the blood treatment device,
   at least one sensor on at least one of the blood loop or the dialysis fluid loop, the sensor being configured to detect and measure a concentration of a first material capable of penetrating the semipermeable membrane, and
   an analysis unit operatively connected to the at least one sensor and configured to determine i) a blood purification performance L1 of the blood purification element for the first material based on the measurement values of the at least one sensor and ii) a blood purification performance L2 of the blood purification element for a second material, which is different from the blood purification performance L1 for the first material, based on data stored in the analysis unit that define a relationship between the blood purification performance L1 for the first material and the blood purification performance L2 for the second material.

2. The blood treatment device according to claim 1, wherein the blood purification performance L is the effective dialysis Deff.

3. The blood treatment device according to claim 2, wherein the analysis unit is configured to derive an effective mass exchange coefficient k0A1eff from a measured dialysance D1eff for the first material, to determine an effective mass exchange coefficient k0A2 eff for the second material from a stored ratio f between a theoretical mass exchange coefficient k0A1th of the second material and a theoretical mass exchange coefficient k0A1th of the first material by multiplying with k0A1eff, and to derive an effective dialysance D2eff for the second material from k0A2eff.

4. The blood treatment device according to claim 2, wherein the analysis unit is configured to derive from a stored theoretical mass exchange coefficient k0A1th for the first material and a stored theoretical mass exchange coefficient k0A2th for the second material, values corresponding thereto for theoretical dialysances D1th and D2th, and to determine an effective dialysance D2eff for the second material from a measured dialysance D1eff for the first material multiplied by a ratio D2th to D1th.

5. The blood treatment device according to claim 1, wherein the at least one sensor is a first downstream sensor on the dialysis fluid removal line and is configured to measure the concentration of the first material in the used dialysis fluid.

6. The blood treatment device according to claim 5, further comprising a dialysis fluid preparation unit connected to the control unit.

7. The blood treatment device according to claim 6, the analysis unit and the control unit being configured to determine the blood purification performance L1 for the first material by a method comprising
   storing a concentration C1di1 of the first material in the fresh dialysis fluid in the analysis unit,
   measuring a concentration C1do1 of the first material in the used dialysis fluid using the first downstream sensor and storing C1do1 in the analysis unit,
   altering a concentration C1di of the first material in the fresh dialysis fluid by the dialysis fluid preparation unit at the command of the control unit,
   storing a changed concentration C1di2 of the first material in the fresh dialysis fluid in the analysis unit,
   measuring a changed concentration C1do2 of the first material in the used dialysis fluid using the first downstream sensor and storing C1do2 in the analysis unit, and
   determining by the analysis unit the blood purification performance L1 on the basis of the concentrations C1di1, C1do1 and changed concentrations C1di2, C1do2 of the first material in the fresh and used dialysis fluid.

8. The blood treatment device according to claim 7, wherein the dialysis fluid preparation unit is configured to perform the change of the concentration C1di in the form of a step or bolus.

9. The blood treatment device according to claim 7, further comprising a first upstream sensor, connected to the analysis unit and located on the dialysis fluid supply line, that is configured to measure the concentrations C1di1 and C1di2 in the fresh dialysis fluid.

10. The blood treatment device according to claim 1, further comprising a second downstream sensor, connected to the analysis unit and located on the dialysis fluid removal line, that is configured to measure the concentration C2do of the second material in the used dialysis fluid.

11. The blood treatment device according to claim 10, wherein the analysis unit is configured to determine a concentration C2bi of the second material in the blood flowing to the second chamber based on the measured concentration C2do of the second material in the used dialysis fluid and the stored concentration C2di of the second material in the fresh dialysis fluid and the established blood purification performance L2 of the second material.

12. The blood treatment device according to claim 1, wherein the first material is sodium.

13. The blood treatment device according to claim 1, wherein the second material is potassium, glucose, creatinine, calcium, or phosphate.

14. A hemodialysis device comprising:
- a blood purification element having a semipermeable membrane, a first chamber connected to a dialysis fluid loop, and a second chamber connected to an extracorporeal blood loop;
- a dialysis fluid supply line to supply fresh dialysis fluid to the first chamber and/or into the blood loop;
- a dialysis fluid removal line to remove used dialysis fluid from the first chamber;
- a control unit to control the hemodialysis device;
- a sensor on the dialysis fluid removal line to measure a concentration of a first material in the used dialysis fluid; and
- an analysis unit operatively connected to the sensor and configured to determine i) a blood purification performance L1 of the blood purification element for the first material based on the measured concentration, and ii) a blood purification performance L2 of the blood purification element for a second material based on data stored in the analysis unit that define a relationship between the performance Li for the first material and the performance L2 for the second material, the performance L2 being different from the performance L1,
- the analysis unit being configured to derive from a stored theoretical mass exchange coefficient k0A1th for the first material and a stored theoretical mass exchange coefficient k0A2th for the second material, values corresponding thereto for theoretical dialysances D1th and D1th, and to determine an effective dialysance D2eff for the second material from a measured dialysance D1eff for the first material multiplied by a ratio D2th to D1th.

15. A hemodialysis device comprising:
- a blood purification element having a semipermeable membrane, a first chamber connected to a dialysis fluid loop, and a second chamber connected to an extracorporeal blood loop;
- a dialysis fluid supply line to supply fresh dialysis fluid to the first chamber and/or into the blood loop;
- a dialysis fluid removal line to remove used dialysis fluid from the first chamber;
- a control unit to control the hemodialysis device;
- a sensor on the dialysis fluid removal line to measure a concentration of a first material in the used dialysis fluid; and
- an analysis unit operatively connected to the sensor and configured to determine i) a blood purification performance L1 of the blood purification element for the first material based on the measured concentration, and ii) a blood purification performance L2 of the blood purification element for a second material based on data stored in the analysis unit that define a relationship between the performance L1 for the first material and the performance L2 for the second material, the performance L2 being different from the performance L1,
- the analysis unit being configured to derive an effective mass exchange coefficient k0A1eff from a measured dialysance D1eff for the first material, to determine an effective mass exchange coefficient k0A2eff for the second material from a stored ratio f between a theoretical mass exchange coefficient k0A2th of the second material and a theoretical mass exchange coefficient kOA1th of the first material by multiplying with k0A1eff, and to derive an effective dialysance D2eff for the second material from k0A2eff.

16. The hemodialysis device according to claim 15, wherein the sensor is configured to detect an electrical conductivity of the first material in the used dialysis fluid.

17. The hemodialysis device according to claim 15, further comprising a second sensor on the dialysis fluid removal line that is configured to measure a concentration of the second material in the used dialysis fluid.

* * * * *

UNITED STATES PATENT AND TRADEMARK OFFICE
CERTIFICATE OF CORRECTION

PATENT NO.       : 7,563,240 B2  
APPLICATION NO.  : 10/552716  
DATED            : July 21, 2009  
INVENTOR(S)      : Gross et al.

Page 1 of 1

It is certified that error appears in the above-identified patent and that said Letters Patent is hereby corrected as shown below:

On the Title Page, item [75], please change "Niederwerm" to --Niederwerrn--.

In the specification:

In column 2, in the formula on lines 62 and 63, please move the "," and place after the "(1)";
In column 3, line 18, please change "a" to --α--;
In column 3, in the formula on lines 47 and 48, please move the "," and place after the "(2)";
In column 9, in the formula on lines 56 and 57, please move the "." and place after the "(5)";
In column 11, in the formula on lines 3 and 4, please move the "," and place after the "(6)"; and
In column 11, in the formula on lines 31 and 32, please move the "," and place after the "(7)".

In the claims:

In column 13, line 64, Claim 3, please change "k0A2 eff" to --k0A2eff--;
In column 13, line 66, Claim 3, please change "k0A1th" to --k0A2th--;
In column 15, line 24, Claim 14, please change "Li" to --L1--;
In column 15, line 32, Claim 14, please change "D1th" to --D2th--; and
In column 16, line 26, Claim 15, please change "kOA1th" to --k0A1th--.

Signed and Sealed this  
Sixth Day of August, 2013

Teresa Stanek Rea  
*Acting Director of the United States Patent and Trademark Office*